US011200242B2

(12) United States Patent
Eda et al.

(10) Patent No.: US 11,200,242 B2
(45) Date of Patent: Dec. 14, 2021

(54) MEDICAL CONDITION COMMUNICATION MANAGEMENT

(71) Applicant: INTERNATIONAL BUSINESS MACHINES CORPORATION, Armonk, NY (US)

(72) Inventors: Sasikanth Eda, Vijayawada (IN); Deepak R. Ghuge, Sangamner (IN); Sandeep R. Patil, Pune (IN); Sachin C. Punadikar, Pune (IN)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 550 days.

(21) Appl. No.: 15/437,555

(22) Filed: Feb. 21, 2017

(65) Prior Publication Data

US 2018/0239873 A1   Aug. 23, 2018

(51) Int. Cl.
*G06F 16/2457* (2019.01)
*G06F 16/248* (2019.01)
*G16H 50/20* (2018.01)
*G16H 70/60* (2018.01)
*G16H 80/00* (2018.01)

(52) U.S. Cl.
CPC ...... *G06F 16/24578* (2019.01); *G06F 16/248* (2019.01); *G16H 50/20* (2018.01); *G16H 70/60* (2018.01); *G16H 80/00* (2018.01)

(58) Field of Classification Search
CPC . G06F 16/24578; G06F 16/248; G16H 80/00; G16H 50/20; G16H 70/60
See application file for complete search history.

(56) References Cited

U.S. PATENT DOCUMENTS

| | | | | |
|---|---|---|---|---|
| 5,879,163 A | * | 3/1999 | Brown | G09B 5/14 |
| | | | | 434/236 |
| 8,255,391 B2 | * | 8/2012 | Kulkarni | G06F 16/951 |
| | | | | 707/723 |
| 8,782,050 B2 | * | 7/2014 | Nelson | G06F 16/31 |
| | | | | 707/740 |
| 9,286,356 B1 | * | 3/2016 | Crichton | G06F 16/24578 |

(Continued)

FOREIGN PATENT DOCUMENTS

| | | |
|---|---|---|
| WO | 2016126678 A1 | 8/2016 |
| WO | WO-2017015392 A1 * | 1/2017 ........... G06F 3/0481 |

*Primary Examiner* — Christopher L Gilligan
*Assistant Examiner* — Chance L Smith
(74) *Attorney, Agent, or Firm* — Griffiths & Seaton PLLC

(57) ABSTRACT

Embodiments for medical condition communication management by one or more processors. A maturity score and medical condition acceptance score relating to a medical condition of a user may be estimated according to data collected from one or more devices associated with the user. The maturity score may represent a measure of an emotional state, age, and cognitive reasoning ability. The medical condition acceptance score may represent a measure of understanding and acceptance capability of the medical condition. One or more search results responsive to a search query related to the medical condition submitted by the user may be adjusted according to the maturity score, the medical condition acceptance score, and an appropriateness of communications for the one or more search results based on a plurality of identified contextual factors.

14 Claims, 10 Drawing Sheets

(56) References Cited

U.S. PATENT DOCUMENTS

| | | | |
|---|---|---|---|
| 2007/0112758 A1 | 5/2007 | Livaditis | |
| 2011/0066607 A1 | 3/2011 | Wong | |
| 2013/0198225 A1 | 8/2013 | Zalis et al. | |
| 2015/0026172 A1 | 1/2015 | Adekile et al. | |
| 2015/0379232 A1* | 12/2015 | Mainwaring | G16H 10/20 |
| | | | 705/2 |
| 2016/0188836 A1* | 6/2016 | Stopek | G06F 19/3481 |
| | | | 705/3 |
| 2018/0025089 A1* | 1/2018 | Chin | G06F 16/337 |
| | | | 707/706 |
| 2018/0144101 A1* | 5/2018 | Bitran | G06F 19/3418 |

* cited by examiner

SEARCH ENGINE | chronic kidney disease

All　News　Apps　Videos　Images　More　Search tools

1. About Chronic Kidney Disease- The National Kidney Foundation
   https://www.kidney.org/kidneydiesease/aboutckd
   Chronic Kidney Disease (CKD) is a condition characterized by a gradual loss of kidney function over time. To read more about kidney function, see How Your...
   Understanding Your Lab Values · Glomerulonephritis · Lupus Nephritis 2. Chronic kidney disease – Treatment – NHS Choices
   Www.nhs.uk/Conditions/Kidney-disease-chronic/Pages/Treatment.aspx
   Your treatment will depend on the stage of your chronic kidney disease (CKD). Stages one, two and three CKD can usually be treated by your GP. Treatment involves making changes to your lifestyle and, in some cases, taking medication. to control your blood pressure and lower your cholesterol levels.

3. Chronic kidney disease – Treatment Overview - WebMD
   www.webmd.com/a-to-z-guides/chronic-kidney-disease-treatment-overview
   Nov 14, 2014 – The goal of treatment for chronic kidney disease is to prevent or slow additional damage to your kidneys.

4. Key Points: Living With Stage 4 Kidney Disease – The National Kidney...
   https://www.kidney.org/patients/peers/stag4
   Chronic kidney disease (CKD) happens if your kidneys have been damaged. ... There is no cure for kidney failure, but with treatment it is possible to live a long, ...

5. Chronic Kidney Disease: What You Can Do - options
   lifeoptions.org > Kidney info
   "The more informed I was, the better I felt about it, I felt I had some control." - CKD patient.

FIG. 6

MEDICAL CONDITION COMMUNICATION MANAGEMENT

BACKGROUND OF THE INVENTION

Field of the Invention

The present invention relates in general to computing systems, and more particularly to, various embodiments for medical condition communication management by one or more processors.

Description of the Related Art

In today's society, consumers, businesspersons, educators, and others communicate over a wide variety of mediums in real time, across great distances, and many times without boundaries or borders. The advent of computers and networking technologies have made possible the intercommunication of people from one side of the world to the other. The increasing complexity of society, coupled with the evolution of technology continues to engender the sharing of a vast amount of information between people. For example, many individuals require extensive use of technology relating to the health and the medical field.

SUMMARY OF THE INVENTION

Various embodiments for medical condition communication management by one or more processors, are provided. In one embodiment, by way of example only, a method for medical condition communication using a conversation planner based on maturity and medical condition capability acceptance scores generated by cognitive medical systems, again by one or more processors, is provided. A maturity score and medical condition acceptance score relating to a medical condition of a user may be estimated according to data collected from one or more devices associated with the user. The maturity score may represent a measure of an emotional state, age, and cognitive reasoning ability. The medical condition acceptance score may represent a measure of understanding and acceptance capability of the medical condition. One or more search results responsive to a search query related to the medical condition submitted by the user may be adjusted according to the maturity score, the medical condition acceptance score, and an appropriateness of communications for the one or more search results based on a plurality of identified contextual factors

BRIEF DESCRIPTION OF THE DRAWINGS

In order that the advantages of the invention will be readily understood, a more particular description of the invention briefly described above will be rendered by reference to specific embodiments that are illustrated in the appended drawings. Understanding that these drawings depict only typical embodiments of the invention and are not therefore to be considered to be limiting of its scope, the invention will be described and explained with additional specificity and detail through the use of the accompanying drawings, in which:

FIG. 6 is a diagram depicting altered search results based upon maturity and medical condition acceptance characteristics by a user for medical condition communication management in accordance with aspects of the present invention in which aspects of the present invention may be realized;

DETAILED DESCRIPTION OF THE DRAWINGS

Figure 1:
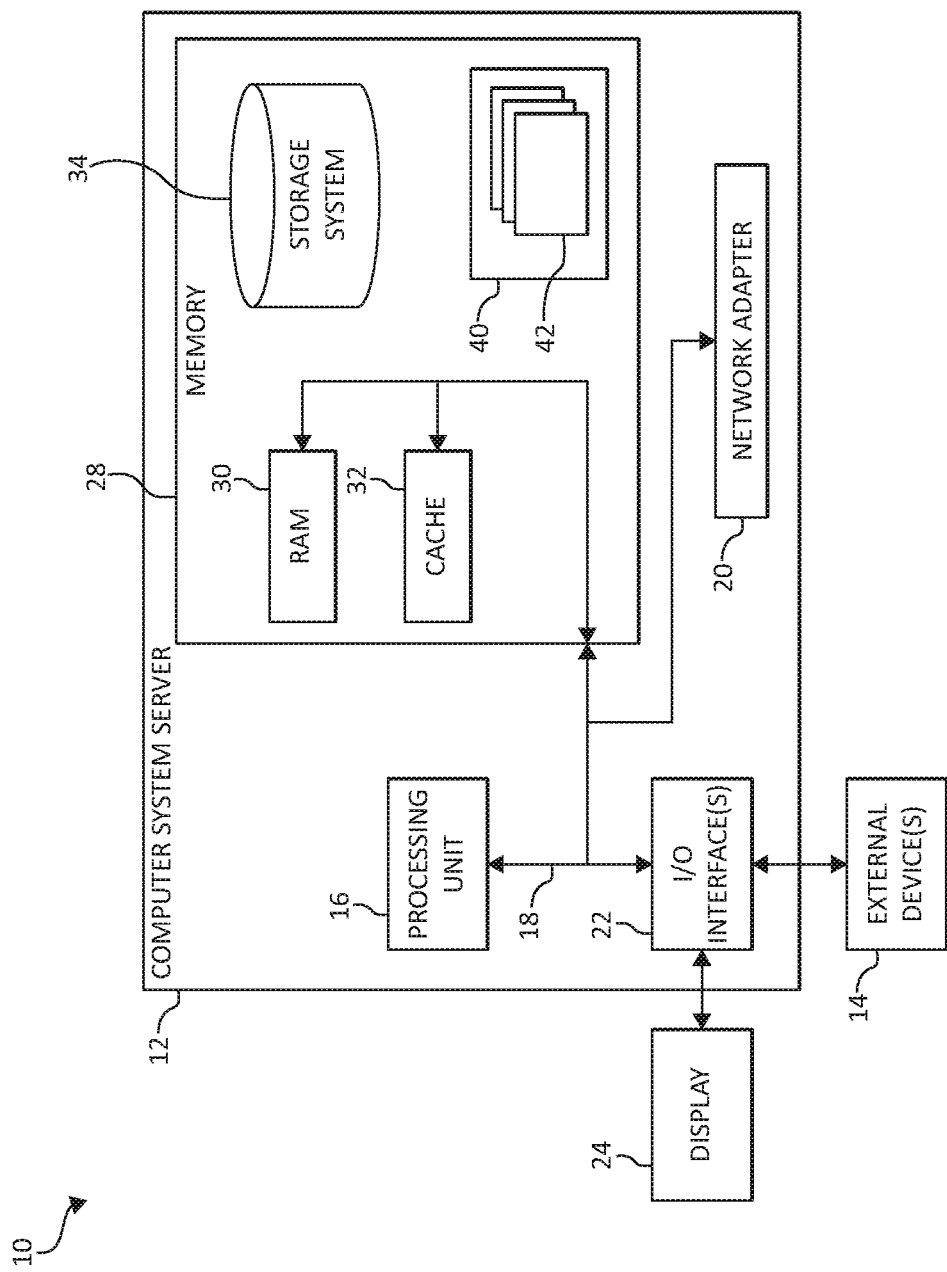
FIG. 1 is a block diagram depicting an exemplary computing node according to an embodiment of the present invention.

As the demand for and level of digital content continues to expand in society, consumers of information content, particularly individuals desiring to gain access to medical information such as, for example, a medical condition and possible outcomes, continue to increase. The openness of the internet with the ever-increasing availability of a variety of types of computing devices for viewing, interacting, or engaging with medical information, provides the ability of users to have continuous access to medical information content.

However, given the sensitivity and emotional response to various types of medical information such as, for example, a medical diagnosis of a disease or debilitating condition, a need exists for increased sensitivity to communicating a medical condition, diagnosis, or medical information to an individual. For example, consider a scenario where an individual, such as a 15 year old (teenage) patient, shows symptoms of vomiting and is admitted to the hospital for the first time since early childhood. In this situation, assume a routine checkup of the individual's kidneys reveals symptoms relating to a medical condition such as, for example, Chronic Kidney Disease (CKD), which is a medical condition characterized by a gradual loss of kidney function over time. In this situation, the doctor may struggle on how and when to deliver to the patient or guardian such medical information given the lack of information relating to maturity and level of understanding and acceptance capability of the patient or guardian.

As an additional example, consider a scenario where the patient has accidentally gained access to and read the observational report relating to the CKD diagnosis prior to the doctor providing a medical explanation. In this case, the curiosity of the patient may motivate the patient to perform individual research and analysis about the medical condition of CKD via the internet, which may conclude with information indicating a non-recoverable, painful future. By reading the displayed search results the negative information and glim medical diagnosis increases fear, reduces courage, loss of hope and generates an emotional state change from calmness to stress, fear, or frustration.

Thus, the present invention provides a solution for medical condition communication based on maturity and medical condition acceptance scores generated by cognitive medical systems, again by one or more processors. A maturity score and medical condition acceptance score relating to a medical condition of a user may be estimated according to data collected from one or more devices associated with the user. The maturity score may represent a measure of an emotional state, age, and cognitive reasoning ability. The medical condition acceptance score may represent a measure of understanding and acceptance capability of the medical condition. One or more search results responsive to a search query related to the medical condition submitted by the user may be adjusted according to the maturity score, the medical condition acceptance score, and an appropriateness of communications for the one or more search results based on a plurality of identified contextual factors.

In one aspect, the present invention provides for using a cognitive medical system (CMS) or clinical decision support system (CDSS), which may be an interactive electronic system that provides guidance for a physician and/or other medical personnel in diagnosing and treating a patient. The CDSS may provide physicians and other health professionals with clinical decision support (CDS), i.e. assistance with clinical decision-making tasks. The CDSS may link health observations with health knowledge to influence health choices by clinicians for improved health care.

In one aspect, a conversation planner may be used for medical condition communication based on maturity and acceptance scores. The conversation planner may be a utility or a template that assists to provide a checklist or preparation workspace for critical meetings or conversations. The conversation planner may include a checklist such as medical history, patient profile, patient intentions, information impact upon a patient, information impact upon a recipient of medication information. The checklist may also include a user "story" or life history/story, recipient life history/story, user intention, information recipient intentions, information impact on the user, information impact on recipient, and/or other selected data.

More specifically, the present invention may estimate a maturity and acceptance characteristics a user of an Internet of Things (IoT) device and change an order/ranking of search results displayed in response to a search query of the user to assist a medical professional in planning an effective conversation with the user (e.g., patient or guardian). That ranking may be based on positive responses and communication relating to the medical condition, medical information, and/or medical diagnostics.

The present invention may provide to a CDSS a collection of data relating to a user (e.g., patient and/or guardian). A maturity score and medical condition acceptance score may be estimated and/or determined. The collection of data may include collecting various data and details of the user (who is performing a search based on one or more observed symptoms) to calculate the maturity and acceptance scores. The various data and details may include, but are not limited to, age, previous medical history (analysis of chronic behaviors), previous medical history of the user's peers and/or colleagues, previous medical history of the user's own family members, one or more goals, career ambitions (analysis of recognitions, organizational profile etc.), user or family financial conditions or status, society impression, type of entertainment (e.g., movies and/or sporting events) the user favors or disfavors (such as when forwarding, sharing or commenting on one or more scenes, events, or circumstances), behavioral data, emotional state data, biomedical data, eating habits, a determination of places of enjoyment or frequently visited locations (e.g., a "hangout"), and/or a measure of places of enjoyment (e.g., a "hangout") levels of enjoyment/preferences of particular locations, social media patterns (e.g., social media behavior patterns such as the various types of social media used, commentary patterns, likes/dislikes of content of social media, and the like), a level or amount of times a user shares feelings with others (e.g., via social media, text, emails, telephonic communication, and/or other forms of communication), a number of emotionally, financially, and/or physically strong/stable associates/peers associated with the user or guardian, and/or information collected by one or more IoT devices or sensors (e.g., wearable devices or sensors.) Each of these parameters may be mined (involve text, video, audio parsers) from various sources and may be ranked against one or more related categories.

In one aspect, in relation to the measure of places of enjoyment, consider for example, a student who may be serious of his/her studies and does not hangout with friends (or hangouts occasionally), attends no movies, has no holiday plans, and likes to stay at home for studies. However, the student thinks/dreams that if he/she could earn a quality wage/money, he/she would be able to visit/tour one or more places "of enjoyment" in the world with the wages/money, perhaps only after he/she is in his/her 40s. Thus, the present invention may also include detecting, measuring, and/or collecting data relating to behavior that postpones certain activities (which may be detected/measured) for some future period of time. The collection of data may include the measure of places of enjoyment. As an additional example, the student may have already visited places and/or frequently visited one or more hangouts. The student does not plan much for future visits and, rather, enjoys each moment of his life rather than planning for the future. In this case, the student may be more or less mature depending on the type of behavior detected and/or analyzed, which may be determined from other behaviors for determining a maturity score.

A weighted value may be assigned and provided as input data to decision mechanisms (e.g., machine learning mechanisms) so as to calculate, estimate, and/or determine a maturity and medical condition acceptance score. In one aspect, calculations, estimates, and/or determinations may be performed using various mathematical operations or functions that may involve one or more mathematical operations (e.g., using addition, subtraction, division, multiplication, standard deviations, means, averages, percentages, statistical modeling using statistical distributions, by finding minimums, maximums or similar thresholds for combined variables, etc.).

A search engine optimization (SEO) operation may be used to provide and/or adjust a ranking of search results (e.g., web pages) based on a positive and/or negative communication (e.g., positive content) in relation to the search results. The ranked search results may be indexed and/or stored. Factors that may be considered for contributing to content positiveness may include, but are not limited to, identified positive comments (e.g., expressing belief, acknowledging success, offering thanks, etc.), usage of positive terminology such as, for example, "cured", "prolonged", and/or "reduced", and the like, explaining a successful story or a statistical result relating to a medical condition.

In one aspect, a conversation planner or preparatory workspace operation may be used to prepare one or more communication points or suggestions which form a background of a user or guardian of the user, conversation notes, a layout based on the web pages ranking that may be altered by a maturity score and medical condition acceptance score.

It should be noted that reference to calculating, determining, setting, and/or estimating a maturity score and medical condition acceptance score may be set as a numerical value, weighted values, and/or an aggregate number of the weighted values that may be compared against the numerical threshold value. In one aspect, calculations or determination operations may be performed using various mathematical operations or functions that may involve one or more mathematical operations (e.g., using addition, subtraction, division, multiplication, standard deviations, means, averages, percentages, statistical modeling using statistical distributions, by finding minimums, maximums or similar thresholds for combined variables, etc.).

Other examples of various aspects of the illustrated embodiments, and corresponding benefits, will be described further herein.

It is understood in advance that although this disclosure includes a detailed description on cloud computing, implementation of the teachings recited herein are not limited to a cloud-computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Referring now to FIG. 1, a schematic of an example of a cloud computing node is shown. Cloud computing node 10 is only one example of a suitable cloud computing node and is not intended to suggest any limitation as to the scope of use or functionality of embodiments of the invention described herein. Regardless, cloud computing node 10 is capable of being implemented and/or performing any of the functionality set forth hereinabove.

In cloud computing node 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 1, computer system/server 12 in cloud computing node 10 is shown in the form of a general-purpose computing device. The components of computer system/server 12 may include, but are not limited to, one or more processors or processing units 16, a system memory 28, and a bus 18 that couples various system components including system memory 28 to processor 12.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, system memory 28 may include at least one program product having a set (e.g., at least one) of program modules that are configured to carry out the functions of embodiments of the invention.

Program/utility 40, having a set (at least one) of program modules 42, may be stored in system memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

Figure 2:
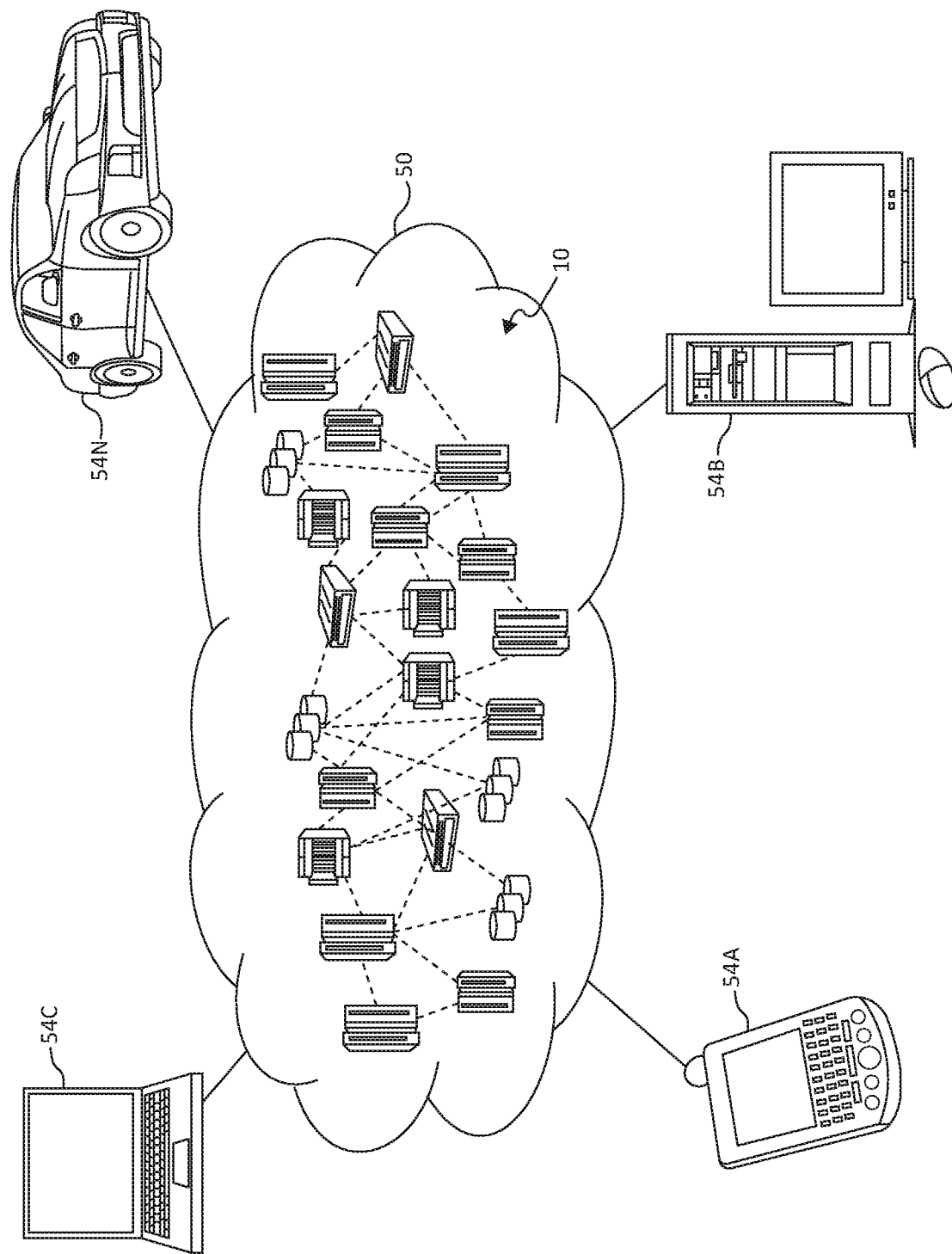
FIG. 2 is an additional block diagram depicting an exemplary cloud computing environment according to an embodiment of the present invention.

Referring now to FIG. 2, illustrative cloud computing environment 50 is depicted. As shown, cloud computing environment 50 comprises one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 2 are intended to be illustrative only and that computing nodes 10 and cloud computing environment 50 can communicate with any type of computerized device over any type of network and/or network addressable connection (e.g., using a web browser).

Figure 3:
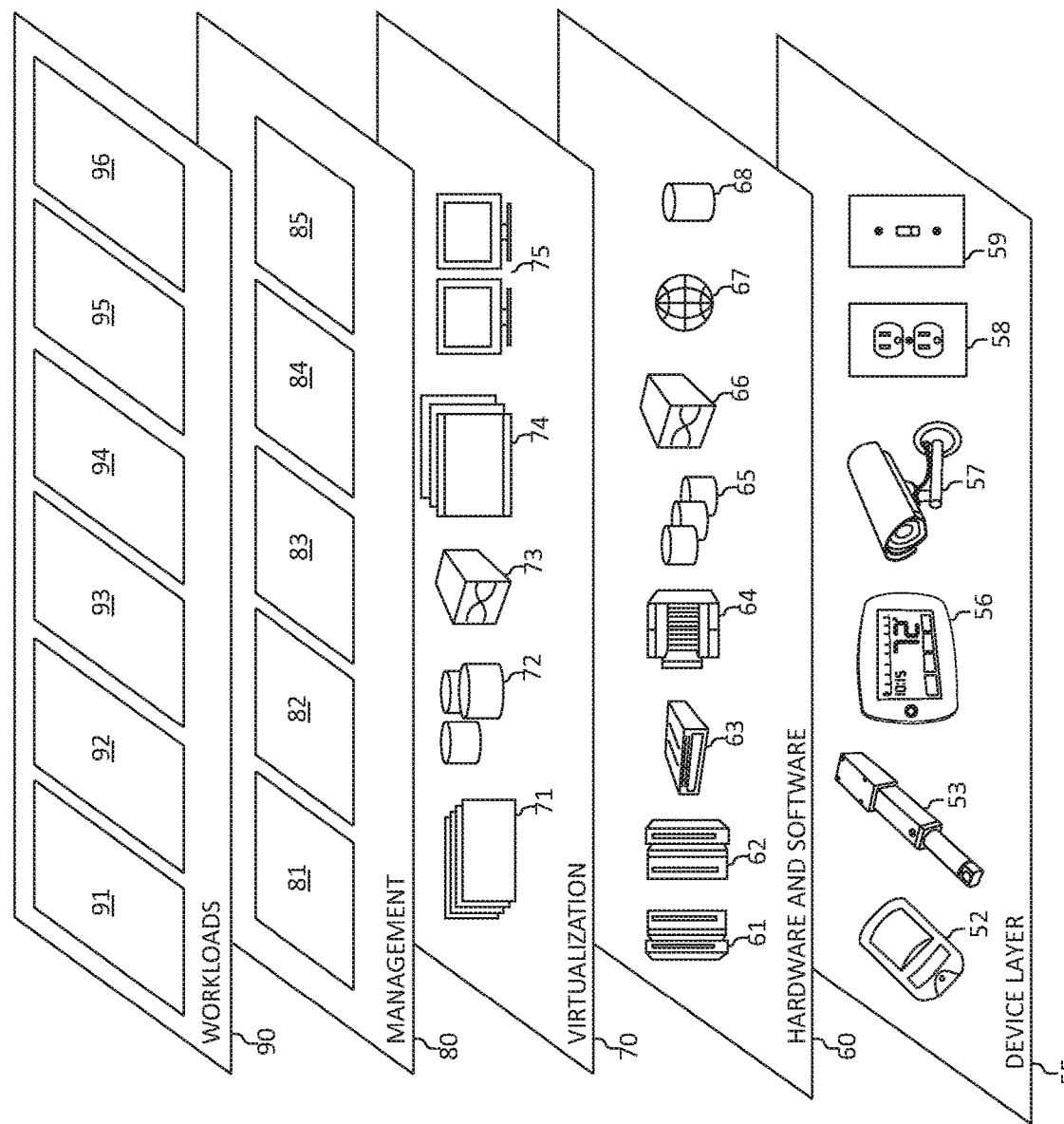
FIG. 3 is an additional block diagram depicting abstraction model layers according to an embodiment of the present invention.

Referring now to FIG. 3, a set of functional abstraction layers provided by cloud computing environment 50 (FIG. 2) is shown. It should be understood in advance that the components, layers, and functions shown in FIG. 3 are intended to be illustrative only and embodiments of the invention are not limited thereto. As depicted, the following layers and corresponding functions are provided:

Device layer 55 includes physical and/or virtual devices, embedded with and/or standalone electronics, sensors, actuators, and other objects to perform various tasks in a cloud computing environment 50. Each of the devices in the device layer 55 incorporates networking capability to other functional abstraction layers such that information obtained from the devices may be provided thereto, and/or information from the other abstraction layers may be provided to the devices. In one embodiment, the various devices inclusive of the device layer 55 may incorporate a network of entities collectively known as the "internet of things" (IoT). Such a network of entities allows for intercommunication, collection, and dissemination of data to accomplish a great variety of purposes, as one of ordinary skill in the art will appreciate.

Device layer 55 as shown includes sensor 52, actuator 53, "learning" thermostat 56 with integrated processing, sensor, and networking electronics, camera 57, controllable household outlet/receptacle 58, and controllable electrical switch 59 as shown. Other possible devices may include, but are not limited to various additional sensor devices, networking devices, electronics devices (such as a remote control device), additional actuator devices, so called "smart" appliances such as a refrigerator or washer/dryer, and a wide variety of other possible interconnected objects.

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provides cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provides pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and, in the context of the illustrated embodiments of the present invention, various medical condition communication management workloads and functions 96. In addition, medical condition communication management workloads and functions 96 may include such operations as data analytics, data analysis, and as will be further described, notification functionality. One of ordinary skill in the art will appreciate that the medical condition communication management workloads and functions 96 may also work in conjunction with other portions of the various abstractions layers, such as those in hardware and software 60, virtualization 70, management 80, and other workloads 90 (such as data analytics processing 94, for example) to accomplish the various purposes of the illustrated embodiments of the present invention.

As previously mentioned, the mechanisms of the illustrated embodiments provide novel approaches for medical condition communication management. A maturity score and medical condition acceptance score relating to a medical condition of a user may be estimated according to data collected from one or more devices associated with the user. One or more search results responsive to a search query related to the medical condition submitted by the user may be adjusted according to the maturity score, the medical condition acceptance score, and an appropriateness of communications for the one or more search results based on a plurality of identified contextual factors.

Figure 4:
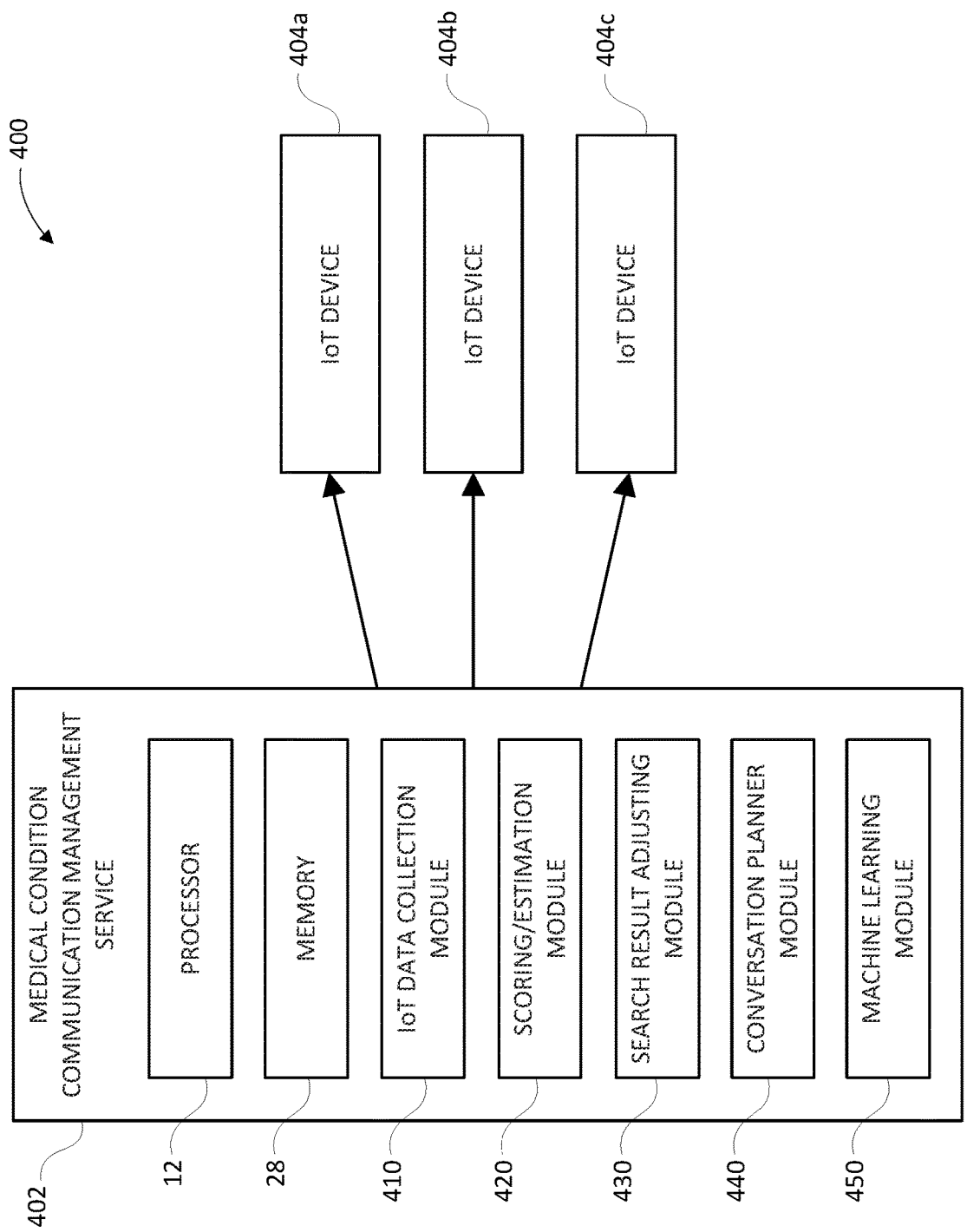
FIG. 4 is an additional block diagram depicting various user hardware and cloud computing components functioning in accordance with aspects of the present invention.

Turning now to FIG. 4, a block diagram depicting exemplary functional components 400 according to various mechanisms of the illustrated embodiments, is shown. As shown, the various functionality, or "modules" of functionality, hardware devices, and/or other components in the same descriptive sense as has been previously described in FIGS. 1-3 may be included in FIG. 4. For example, processing unit 12 and memory 28 of FIG. 1 may be employed in FIG. 4 to perform various computational, data processing, storage and other functionality in accordance with various aspects of the present invention.

The system 400 may include functional components such as a medical condition communication management service 402, having an IoT device data collection module 410, a scoring and/or estimation ("scoring/estimation") module 420, a search result adjusting module 430, a conversation planner module 440, and a machine learning module 450, each of which may work in communication with each other.

The medical condition communication management service 402 may be in communication with one or more IoT devices 404 (illustrated as 404a-c in FIG. 4). The medical condition communication management service 402 may determine performance capabilities, functions, services, and/or other functionality of each IoT device, such as IoT devices 404a-c, combination of IoT devices, and/or a computing network (e.g., an IoT network) as depicted herein. The medical condition communication management service 402 may use a cognitive medical system (CMS) or a clinical decision support system (CDSS) application.

The IoT device data collection module 410 may be used to harvest, collect, and store data. The machine learning module 450 may continuously and automatically receive from one or more IoT devices, such as IoT devices 404a-c, feedback according to medical condition communication management service 402 applications for each user. In one aspect, the IoT devices, such as IoT devices 404a-c may be a sensor device that may read, detect, store, and/or harvest data. The IoT device data collection module 410 may determine whether or not each of the IoT devices 404a-c are compliant or non-complaint according to the created set of constraints of the one or more media policies and control rules/applications.

The IoT device data collection module 410 may parse through the collected data from one or more of the IoT devices, such as IoT devices 404a-c which may be "wearable" devices, associated with the user to identify one or more categories that includes identifying an age of the user, medical history, medical history of one or more persons associated with the user, financial conditions, status of employment, a social media user profile, social media communication patterns, favorable and unfavorable entertainment interests, food preferences, profile types and characteristics of persons associated with the user, an emotional state of the user, biometric data, behavior patterns, or a combination thereof.

The scoring/estimation module 420 may estimate a maturity score and medical condition acceptance score relating to a medical condition of a user according to data collected from one or more devices associated with the user such as, for example, each of the IoT devices 404a-c. The scoring/estimation module 420 may assign a weighted value to each of the one or more categories for estimating the maturity score and the medical condition acceptance score, wherein the assigned weighted values may be ranked. For example, scoring/estimation module 420 may rank the one or more search results based on the maturity score, the medical condition acceptance score, and the appropriateness of the communications based on the plurality of identified contextual factors.

The scoring/estimation module 420 may also apply one or more selected rules for a set of the one or more categories for estimating the maturity score and the medical condition acceptance score. The scoring/estimation module 420 may estimate, calculate, determine and/or set the maturity score and/or the medical condition acceptance score to a value within a range of values. The range of values include at least values representing a measure of an emotional state, age, and cognitive reasoning ability for the maturity score and a measure of understanding and acceptance capability of the medical condition for the medical condition acceptance score.

For example, consider the feature set and identification criteria per feature set, which may be minded and parsed (text, audio, video parsed) from a user's data that is collected from various sources illustrated by one or more operations. A feature set may include age. The behavior identified relating to age may include 1) a "$C_{1-1}$" operation to parse and identify an age group of the user (patient/guardian) based on the type of tweets/posts, person tagged in photographs uploaded, etc., and/or 2) a "$C_{1-2}$" operation to parse and identify a generalized maturity of the identified age group, as well as a generation behavior of peers of the user.

A feature set may include previous medical history. The behavior identified relating to previous medical history may include 1) a "$C_{2-1}$" operation to parse and identify a chronic history from Person Health Information ("PHI"), and/or 2) a "$C_{2-2}$" operation to parse and identify a number of visits to hospital, any admitted history, long term usage of medicines, etc.

A feature set may include a previous medical history of the user's peers/colleagues. The behavior identified relating to previous medical history may include 1) a "$C_{3-1}$" operation to parse and identify if peers/colleagues went to a hospital or location seeking medical help or assistance where the user is now being treated, and/or 2) a "$C_{3-2}$" operation to parse and identify any incident, parse to identify the severity of peer/colleague's medical condition along with counting number of visits, stay type (which may be used to identify if user stayed in hospital along with admitted person), dates (which may be used to identify if it is recent or not), or a combination thereof.

A feature set may include a previous medical history of the user's own family members associated with the user. The behavior identified relating to previous medical history may include 1) a "$C_{4-1}$" operation to parse and identify if any family members went to a hospital or location seeking medical help or assistance where the user is now being treated, and/or 2) a "$C_{4-2}$" operation to parse and identify a severity of a family member's medical condition along with counting number of visits, stay type (which may be used to identify if user stayed in hospital along with admitted person), dates (which may be used to identify if it is recent or not), or a combination thereof.

A feature set may include current career ambitions (accessed based on the recent awards, etc.). The behavior identified relating to current career ambitions may include a "$C_{5-1}$" operation to parse and identify the user's recent achievements, awards (e.g., academic, professional, governmental, economical, etc.), career progressions, recommendations made by others in a social network, organization collaboration pages, or other data relating to a career or employment.

A feature set may include family financial conditions/economic status. The behavior identified may include a "$C_{6-1}$" operation to estimate the user's financial status by parsing and identifying a purchase history of one or more of the family members (along with type of products and their classification), recommendations made by online shopping, real estate purchases, vacations, rental properties, vehicle purchases, leases, or rental history, retirement accounts, investments, insurance, and/or a plurality of other financial platforms.

A feature set may include society impressions. The behavior identified may include a "$C_{7-1}$" operation to identify user behavior relating to charities, one or more activities contributing to the development of society or community (e.g., volunteer activities relating to church, government, non-profit groups, etc.), participation in environment awareness programs, and/or a plurality of other activities relating to society/community involvement or awareness.

A feature set may include types of entertainment such as, for example, sporting events, plays, operas, recreational activities, movies that the user liked in the past (e.g., such as movie clips shared with a social network or "likes" on a social media platform). For example, the behavior identified may include 1) a "$C_{8-1}$" operation to parse to identify the user's most watched videos or events such as, for example, educational documentaries, "Ted talks", videos and/or media relating to one or more various categories, and/or 2) a "$C_{8-2}$" operation to parse and identify a type of scene/event which the user tends to skip or fast forward and types of scenes most watched by user.

A feature set may include food habits. The behavior identified may include a "$C_{9-1}$" operation to parse to identify a type and nature of food preferred or liked by the user (such as for determining if the user is healthy enough with a particular diet or wants to try out new recipes, etc.). The identification may be done based on number of food serving places visited (e.g., restaurant or cafeteria) by the user, comments made on the dishes, and/or reviews provided in a social network or online-community or website that encourages or solicits reviews or commentary.

A feature set may include a level of enjoyment relating to an event or activity. The behavior identified may include 1) a "$C_{10-1}$" operation to parse to identify types of events attended or engaged in and/or preferred to be attended by the user, and/or 2) a "$C_{10-2}$" operation to parse to identify the usual weekend routines of the user (places user visits over weekend, etc.).

A feature set may include a level of sharing feelings with others. The behavior identified may include 1) a "$C_{11-1}$" operation to parse to identify types of online communication posts/"tweets" that are shared by the user, 2) a "$C_{11-2}$" operation to parse to identify the conversation durations (both in terms of text, audio, video, etc.), and/or 3) a "$C_{11-3}$" operation to parse a social network profile to identify if the user has an introvert or extrovert nature.

A feature set may include a number of physically strong/stable associates/peers associated with the user or guardian. The behavior identified may include 1) a "$C_{12-1}$" operation to parse on medical records (e.g., hospital management records) to identify a number of visitors to the hospital or medical facilities along with the time duration spent with the user, 2) a "$C_{12-2}$" operation to parse to identify a user's maturity in terms of handling real time situations based on one or more feature sets as described herein, and/or 3) a "$C_{12-3}$" operation to parse and identify a number of executives (e.g., chief executive officer 'CEO' and the like) connected with the user.

A feature set may include a data or "details" relating to the user based upon the data and/or details obtained via one or more IoT sensors. The behavior identified may include a "$C_{13-1}$" operation to parse to identify sensor details collected by various wearable devices used by the user to identify the accurate daily routines (like time spent in workouts, conscious on fitness, etc.) and emotion quotient (like laughter, sadness, etc., which can be measured using heart rate data).

Accordingly, based upon the above description (such as for the feature set(s)), each feature set (which may be a function of time) may be comprised on multiple sub rules which determine the user characteristics per feature set. A linear weighted approximation model can be applied per feature set, wherein each of the operation sets of $C_{1-1}$-$C_{13-1}$ may include one or more functions of times depicted as one or more of the following equations:

$$f_1(t)=w_{1-1}*C_{1-1}+w_{1-2}*C_{1-2}$$

$$f_2(t)=w_{2-1}*C_{2-1}+w_{2-2}*C_{2-2}$$

$$f_3(t)=w_{3-1}*C_{3-1}+w_{3-2}*C_{3-2}$$

$$f_4(t)=w_{4-1}*C_{4-1}+w_{4-2}*C_{4-2}$$

$$f_5(t)=w_{5-1}*C_{5-1}$$

$$f_6(t)=w_{6-1}*C_{6-1}$$

$$f_7(t)=w_{7-1}*C_{7-1}$$

$$f_8(t)=w_{8-1}*C_{8-1}+w_{8-2}*C_{8-2}$$

$$f_9(t)=w_{9-1}*C_{9-1}$$

$$f_{10}(t)=w_{10-1}*C_{10-1}+w_{10-2}*C_{10-2}$$

$$f_{11}(t)=w_{11-1}*C_{11-1}+w_{11-2}*C_{11-2}+w_{11-3}*C_{11-3}$$

$$f_{12}(t)=w_{12-1}*C_{12-1}+w_{12-2}*C_{12-2}+w_{12-3}*C_{12-3}$$

$$f_{13}(t)=w_{13-1}*C_{13-1},$$

where $C_{1-1}$, $C_{1-2}$, $C_{13-1}$ are binary values and if data or evidence related to each selected or defined sub rule is identified they are represented with value "1" and if not found are represented with value "0". The weights, for example, may be assigned a value such as for example, where $w_{1-1}=10$, $w_{1-2}=5$, $w_{2-1}=10$, $w_{2-2}=10$, $w_{3-1}=15$, $w_{3-2}=20$, $w_{4-1}=5$, $w_{4-2}=10$, $w_{5-1}=20$, $w_{6-1}=5$, $w_{7-1}=5$, $w_{8-1}=10$, $w_{8-2}=10$, $w_{9-1}=5$, $w_{10-1}=10$, $w_{10-2}=10$, $w_{11-1}=20$, $w_{11-2}=5$, $w_{11-3}=5$, $w_{12-1}=10$, $w_{12-2}=10$, $w_{12-3}=5$, $w_{13-1}=5$. These weights may be assigned, altered, and/or generated based on the importance or priority of the sub rules. It should be noted that each of the feature sets may be one or more of the plurality of identified contextual factors. One or more of the feature sets may be used to estimate, determine, or calculate the maturity score and/or the medical condition acceptance score.

In one aspect, one or more additional rules involved to identify each sub rule may be added together such as, for example, a "$C_{2-1}$" operation may be added to one or more sub rules to parse and identify a chronic history from Person Health Information ("PHI"), which may involve multiple sub rules within "$C_{2-1}$", which can be details collected and/or parsed from one or more IoT devices or other data sources. The IoT devices and data sources may include wearable devices, details collected and/or parsed from social media, details collected and/or parsed from businesses, organizations, medical organizations or business, scientific institutions, academic institutions, and/or other industries or services.

The search result adjusting module 430 may adjust one or more search results responsive to a search query related to the medical condition submitted by the user according to the maturity score, the medical condition acceptance score, and an appropriateness of communications for the one or more search results based on a plurality of identified contextual factors. Moreover, the search result adjusting module 430 may cognitively interpret the appropriateness of the communications (of one or more search results prior to the adjusting) based on the plurality of identified contextual factors (e.g., feature sets) by interpreting comments, reviews, medical condition outcomes, positive responses to the medical condition, terminology (each of which are part of the contextual factors) in view of the communications. In association with the scoring/estimation module 420, the search result adjusting module 430 may rank and adjust one or more search results using the maturity score, the medical condition acceptance score, and the cognitively interpreted communications.

The conversation planner module 440 may be used for collecting the adjusted search results and providing one or more suggestions for communication with the user according to the adjusted one or more search results, the maturity score, and the medical condition acceptance score. That is, the conversation planner module 440 may prepare one or more talking points or communication suggestions based upon the adjusted one or more search results, the maturity score, and the medical condition acceptance score.

The machine learning module 450 may be used to track, monitor, and analyze feedback relating to the IoT devices, such as IoT devices 404a-c relating to the estimating and adjusting of the search results. For example, the machine learning module 450 may collect and learn behavioral data over a course of a selected time period to assist with estimating the maturity score, the medical condition acceptance score, and adjusting one or more search results responsive to a search query related to the medical condition submitted by the user. The learned behavioral data may include, for example, learning and interpreting user information (e.g., age, medical history, finances, employment status, emotional state, social media patterns, communications discussing an emotional state or well-being, habits, lifestyle, etc.).

The IoT device data collection module 410 and/or machine learning module 450 may include using one or more heuristics and machine learning based models for performing one or more of the various aspects as described herein. In one aspect, the IoT device compliance service and machine learning based models may be performed using a wide variety of methods or combinations of methods, such as supervised learning, unsupervised learning, temporal difference learning, reinforcement learning and so forth. Some non-limiting examples of supervised learning which may be used with the present technology include AODE (averaged one-dependence estimators), artificial neural network, back propagation, Bayesian statistics, naive bays classifier, Bayesian network, Bayesian knowledge base, case-based reasoning, decision trees, inductive logic programming, Gaussian process regression, gene expression programming, group method of data handling (GMDH), learning automata, learning vector quantization, minimum message length (decision trees, decision graphs, etc.), lazy learning, instance-based learning, nearest neighbor algorithm, analogical modeling, probably approximately correct (PAC) learning, ripple down rules, a knowledge acquisition methodology, symbolic machine learning algorithms, sub symbolic machine learning algorithms, support vector machines, random forests, ensembles of classifiers, bootstrap aggregating (bagging), boosting (meta-algorithm), ordinal classification, regression analysis, information fuzzy networks (IFN), statistical classification, linear classifiers, fisher's linear discriminant, logistic regression, perceptron, support vector machines, quadratic classifiers, k-nearest neighbor, hidden Markov models and boosting. Some non-limiting examples of unsupervised learning which may be used with the present technology include artificial neural network, data clustering, expectation-maximization, self-organizing map, radial basis function network, vector quantization, generative topographic map, information bottleneck method, IBSEAD (distributed autonomous entity systems based interaction), association rule learning, apriori algorithm, eclat algorithm, FP-growth algorithm, hierarchical clustering, single-linkage clustering, conceptual clustering, partitional clustering, k-means algorithm, fuzzy clustering, and reinforcement learning. Some non-limiting example of temporal difference learning may include Q-learning and learning automata. Specific details regarding any of the examples of supervised, unsupervised, temporal difference or other machine learning described in this paragraph are known and are considered to be within the scope of this disclosure. Also, when deploying one or more machine learning models, a computing device may be first tested in a controlled environment before being deployed in a public setting. Also even when deployed in a public environment (e.g., external to the controlled, testing environment), the computing devices may be monitored for compliance.

Figure 5A:
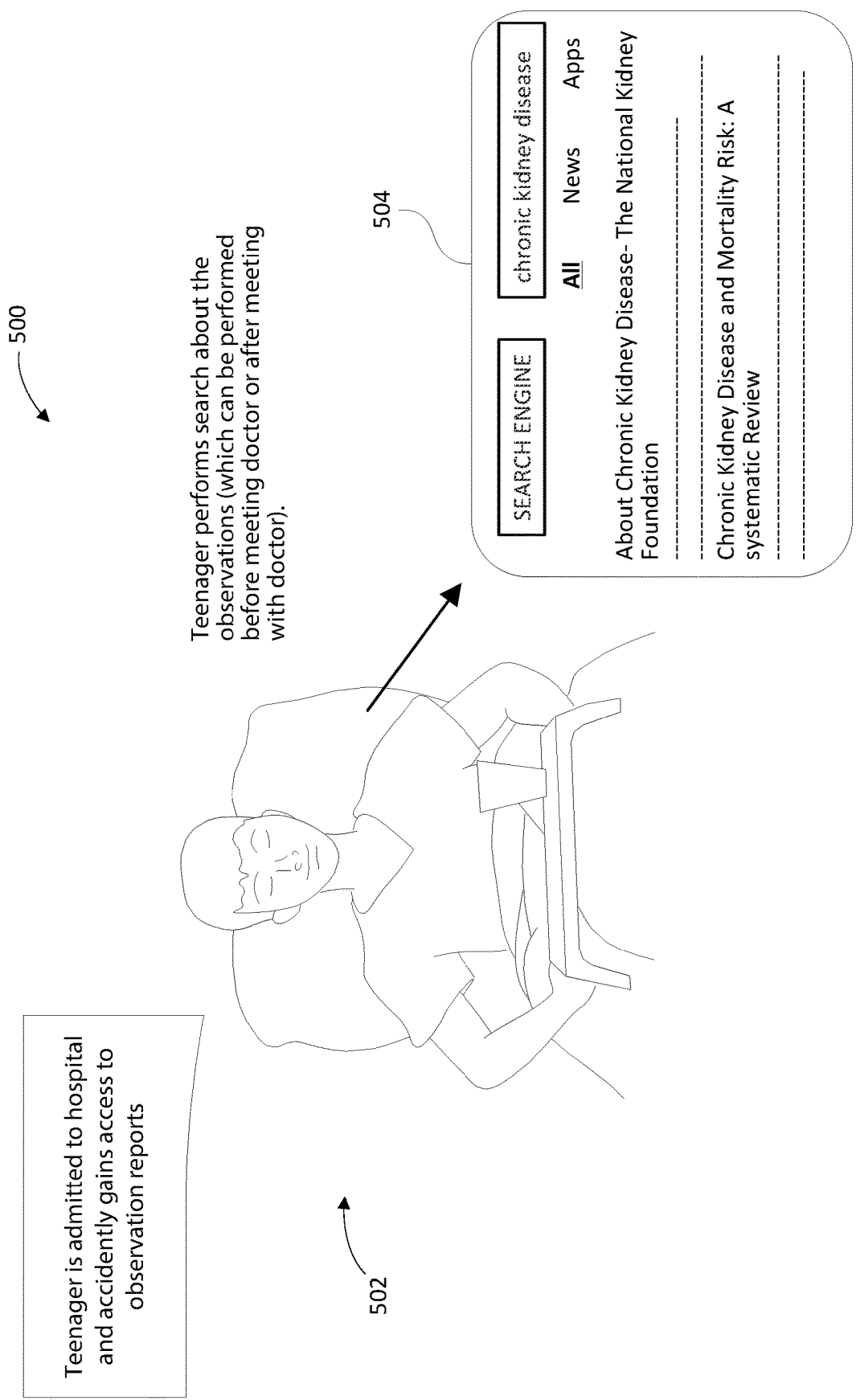
FIG. 5A-B are diagrams depicting search results responsive to a search query by a user in accordance with aspects of the present invention.
Figure 5B:
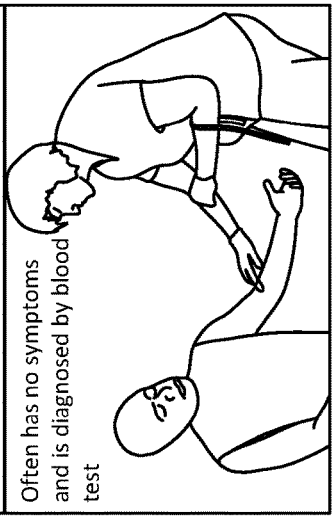

In view of the various embodiments described herein, consider an illustration of FIG. 5A-5B that depicts search results responsive to a search query by a user 502. As depicted, a user (e.g., a patient or guardian) may gain access to and observe a medical observation report. Assume, for illustration purposes, the user is a teenager around the age of 15. Assuming, for illustration purposes, the medical observation report or symptoms reveals a medical condition relating to, for example, Chronic Kidney Disease (CKD). As an additional aspect, consider as part of the example, the user/patient has accidentally gained access to and read the observational report relating to the CKD diagnosis prior to the doctor providing a medical explanation.

In this case, the curiosity of the patient may motivate the patient to perform individual research and analysis about the medical condition such as, for example, CKD, via the internet which may conclude with information indicating a non-recoverable, painful future. The user may use an IoT device (such as a computer, laptop, smartphone, tablet, smart watch, or other device or sensor device) to perform a search query relating to information or symptoms indicated in the medical observation report relating to a medical condition and/or personally observed symptoms of the medical condition. However, the search query does not consider a maturity level (e.g., emotional state, age, or cognitive reasoning ability) of the user to accept the search results 504, which may include negative data (illustrated in FIG. 5B as the negative communication such as "a gradual loss of kidney function over time"). By reading the displayed search results 504, the negative and glim medical diagnosis increases fear, reduces courage, loss of hope and generates huge stress.

Accordingly, to address the negative display of results of FIG. 5A-5B, FIG. 6 depicts altered search results based upon maturity and medical condition acceptance characteristics by a user for medical condition communication management. Here, maturity score and medical condition acceptance score relating to a medical condition of a user are estimated according to data collected from one or more devices associated with the user. Upon performing the estimation, the search results responsive to the search query related to the medical condition submitted by the user may be adjusted according to the maturity score, the medical condition acceptance score, and an appropriateness of communications for the one or more search results based on a plurality of identified contextual factors. Machine learning operations may be implemented to learn and analyze information relating to the maturity and medical condition acceptance capabilities of a user. For example, the machine learning operations may learn and analyze information relating to the maturity and medical condition acceptance capabilities of a user and estimate a maturity and medical condition acceptance capabilities score. Also, machine learning operations may collect comments/feedback about medical conditions, including personal experiences from other users or patients, to determine the sentiment (positive or negative) of the experiences. Such feedback may be supplied to a medical condition database accessible for assisting in readjusting search results based upon a maturity and medical condition acceptance capabilities score.

The identified contextual factors may include one or more user defined parameters and/or comments, reviews, medical condition outcomes, positive responses to the medical condition, and terminology in view of the communications such as, for example, the negative communication illustrated in FIG. 6 as dotted-underlined text (e.g., "a gradual loss of kidney function over time") and positive communication illustrated in FIG. 6 as bold-underlined text (e.g., "but with treatment it is possible to live a long . . . "). The identified contextual factors may include an age of the user, medical history, medical history of one or more persons associated with the user, financial conditions, status of employment, a social media user profile, social media communication patterns, favorable and unfavorable entertainment interests, food preferences, profile types and characteristics of persons associated with the user, an emotional state of the user, biometric data, behavior patterns, or a combination thereof.

Figure 7:
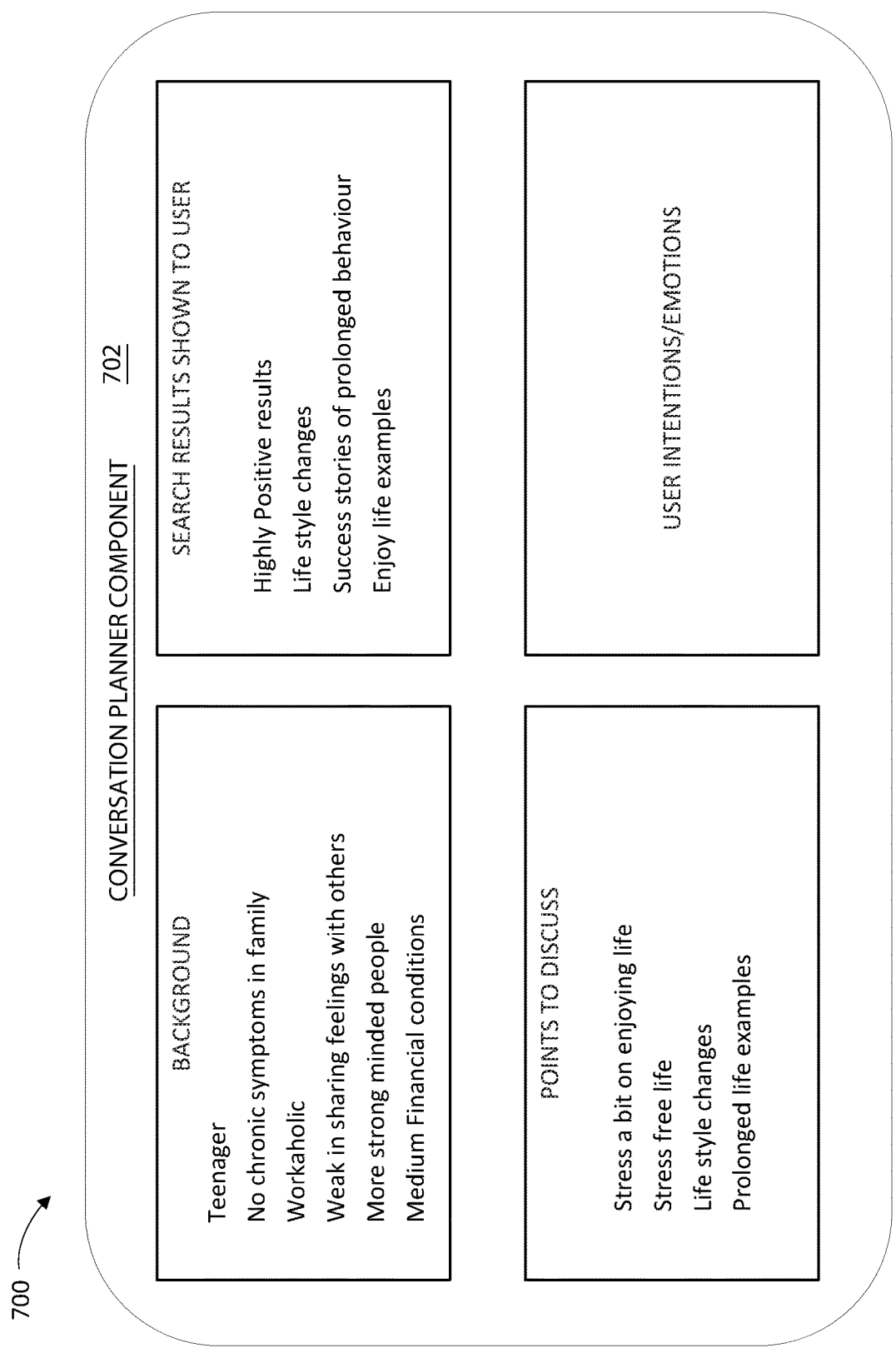
FIG. 7 is a diagram depicting a conversation planner workspace for medical condition communication management in accordance with aspects of the present invention in which aspects of the present invention may be realized.

Turning now to FIG. 7, a conversation planner component 702 is displayed which provides a conversation planner workspace. It should be noted that the various functionality, or "modules" of functionality, hardware devices, and/or other components in the same descriptive sense as has been previously described in FIGS. 1-6 may be included in FIG. 7. For example, processing unit 12 and memory 28 of FIG. 1 may be employed in FIG. 7 to perform various computational, data processing, storage and other functionality in accordance with various aspects of the present invention.

In one aspect, the conversation planner component 702 provides a conversation planner workspace for medical condition communication management. Upon adjusting the search results, the conversation planner component 702 may be used to provide one or more suggestions for communication with the user according to the adjusted one or more search results, the maturity score, and the medical condition acceptance score. As depicted, the conversation planner workspace may include a background, search results shown to a user, points to discuss (e.g., communication suggestions), and/or user intentions/emotions. The conversation planner workspace may be communicated to one or more medical professionals such as, for example, sending via a communication network the conversation planner via a cognitive medical system (CMS) or clinical decision support system (CDSS), which may be an interactive electronic system that provides guidance for some physicians or other medical personnel in diagnosing and treating a patient.

Figure 8:
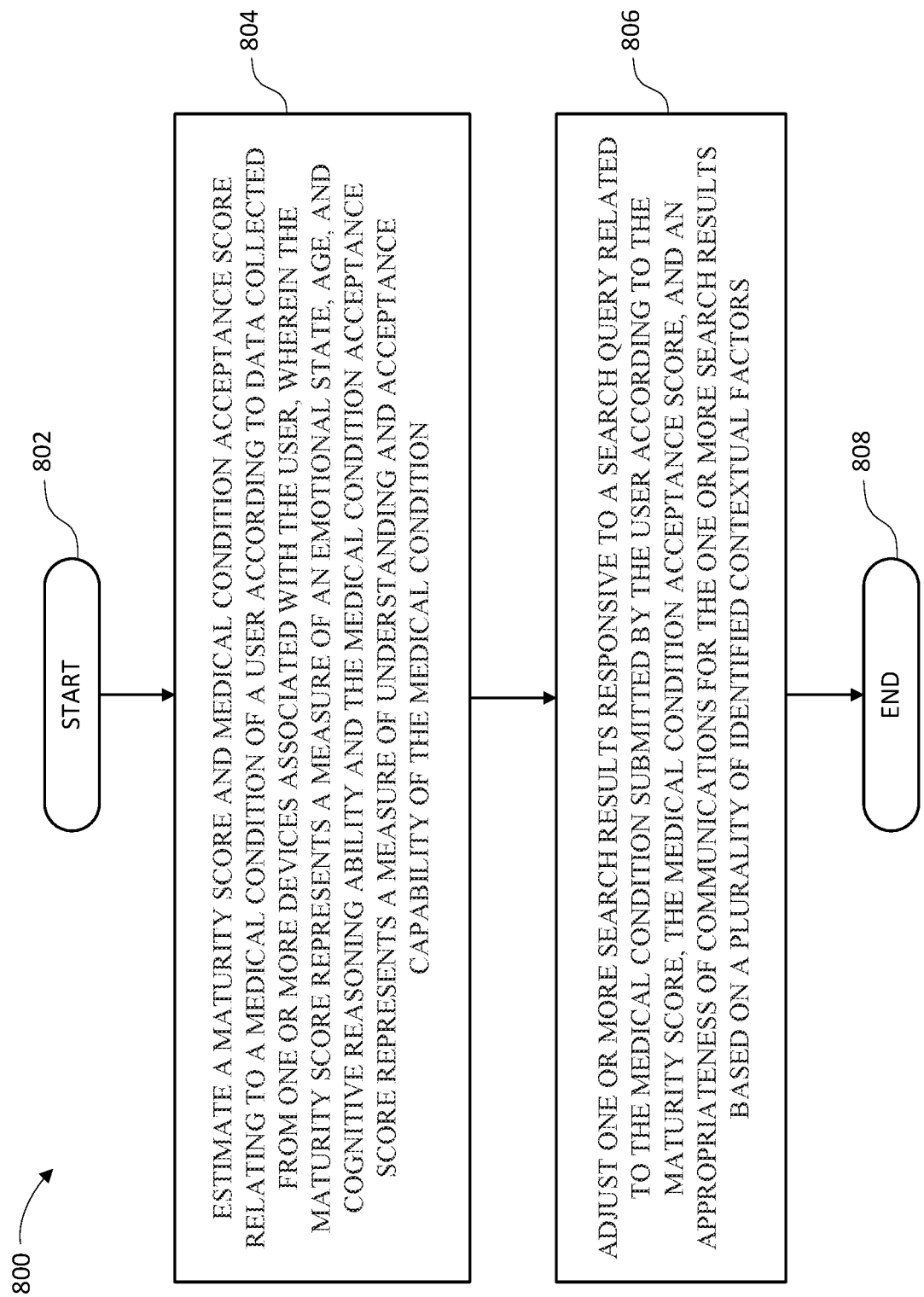
FIG. 8 is a flowchart diagram depicting an additional exemplary method for medical condition communication management by one or more processors in which aspects of the present invention may be realized.

Turning now to FIG. 8, a method 800 for medical condition communication management by one or more processors is depicted, in which various aspects of the illustrated embodiments may be implemented. The functionality 800 may be implemented as a method executed as instructions on a machine, where the instructions are included on at least one computer readable medium or one non-transitory machine-readable storage medium. The functionality 800 may start in block 802. A maturity score and medical condition acceptance score relating to a medical dawn of a user may be estimated according to data collected from one or more devices associated with the user, wherein the maturity score represents a measure of an emotional state, age, and cognitive reasoning ability and the medical condition acceptance score represents a measure of understanding and acceptance capability of the medical condition, as in block 804. One or more search results responsive to a search query related to the medical condition submitted by the user may be adjusted according to the maturity score, the medical condition acceptance score, and an appropriateness of communications for the one or more search results based on a plurality of identified contextual factors, as in block 806. The functionality 800 may end, as in block 808.

Figure 9:
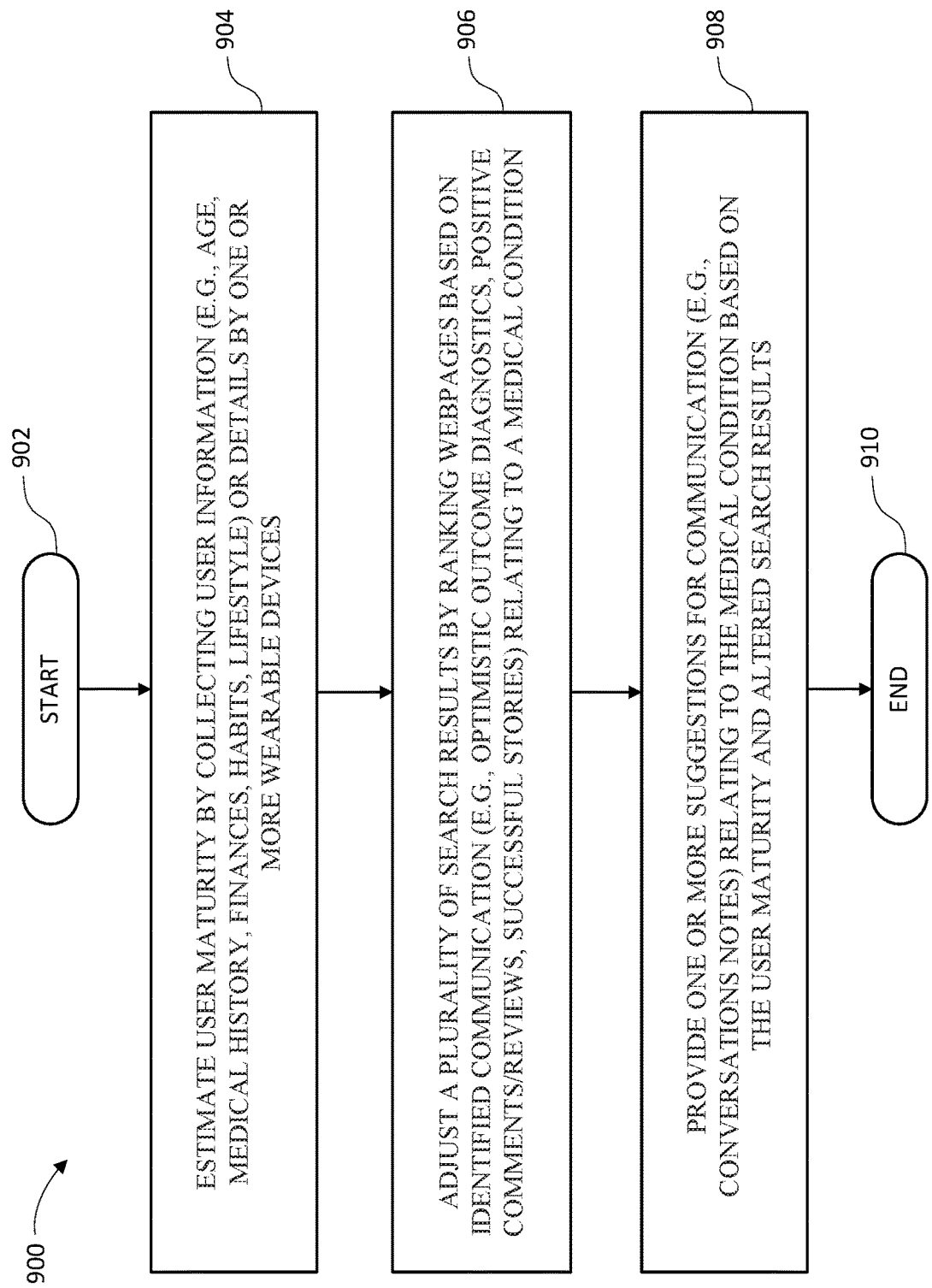
FIG. 9 is a flowchart diagram depicting an additional exemplary method for medical condition communication management by one or more processors, again in which aspects of the present invention may be realized.

Turning now to FIG. 9, a method 900 for medical condition communication management by one or more processors is depicted, in which various aspects of the illustrated embodiments may be implemented. The functionality 900 may be implemented as a method executed as instructions on a machine, where the instructions are included on at least one computer readable medium or one non-transitory machine-readable storage medium. The functionality 900 may start in block 902. A user maturity (e.g., a maturity level of a "patient" using one or more IoT devices) may be estimated by collecting user information (e.g., age, medical history, finances, employment status, emotional state, social media patterns, communications discussing an emotional state or well-being, habits, lifestyle, etc.) by one or more wearable devices (e.g., an IoT device), as in block 904. A plurality of search results may be readjusted by ranking webpages based on identified communication (e.g., optimistic outcome diagnostics, positive comments/reviews, successful stories relating to medical conditions, procedures, and/or diagnosis) relating to a medical condition, as in block 906. One or more suggestions may be provided for communication (conversations notes) relating to the medical condition based on the user maturity and altered search results, as in block 908. The functionality 900 may end, as in block 910.

In one aspect, in conjunction with and/or as part of at least one block of FIGS. 8 and 9, the operations of methods 800 and/or 900 may include each of the following. The operations of methods 800 and/or 900 may provide one or more suggestions for communication (e.g., talking points provided by a conversation planner) with the user according to the adjusted one or more search results, the maturity score, and the medical condition acceptance score. Data collected from one or more wearable devices associated with the user may be parsed to identify one or more categories that includes identifying an age of the user, medical history, medical history of one or more persons associated with the user, financial conditions, status of employment, a social media user profile, social media communication patterns, favorable and unfavorable entertainment interests, food preferences, profile types and characteristics of persons associated with the user, an emotional state of the user, biometric data, behavior patterns, or a combination thereof.

The operations of methods 800 and/or 900 may assign a weighted value to each of the one or more categories for estimating the maturity score and the medical condition acceptance score, wherein the assigned weighted values are ranked, and/or apply one or more selected rules for a set of the one or more categories for estimating the maturity score and the medical condition acceptance score. An appropriateness of the communications may be cognitively interpreted based on the plurality of identified contextual factors by interpreting comments, reviews, medical condition outcomes, positive responses to the medical condition, and terminology in view of the communications.

The operations of methods 800 and/or 900 may rank the one or more search results based on the maturity score, the medical condition acceptance score, and the appropriateness of the communications based on the plurality of identified contextual factors.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowcharts and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowcharts and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowcharts and/or block diagram block or blocks.

The flowcharts and block diagrams in the Figures illustrate the architecture, functionality, and operation of possible implementations of systems, methods, and computer program products according to various embodiments of the present invention. In this regard, each block in the flowcharts or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustrations, and combinations of blocks in the block diagrams and/or flowchart illustrations, can be implemented by special purpose hardware-based systems that perform the specified functions or acts or carry out combinations of special purpose hardware and computer instructions.

The invention claimed is:

1. A method for medical condition communication management by one or more processors, comprising:
   collecting, by the one or more processors, data from one or more devices associated with a user, wherein when collecting the data, a plurality of sources are mined by the one or more devices using textual, audio, and video parsers such that the data is collected notwithstanding whether the user explicitly entered the data into the one or more devices;
   training, by the one or more processors, a machine learning model using the collected data from the one or more devices, wherein training the machine learning model includes identifying a plurality of feature sets within the collected data that are each representative of characteristics of the user including medical background information of the user, activities engaged in by the user, and content consumed by the user on the one or more devices;
   estimating, by the one or more processors, a maturity score and medical condition acceptance score relating to a medical condition of the user according to the collected data as analyzed in the plurality of feature sets by the trained machine learning model, wherein the maturity score represents a measure of an emotional state, age, and cognitive reasoning ability, and wherein the medical condition acceptance score represents a measure of understanding and acceptance capability of the medical condition; and
   automatically adjusting one or more search results of a plurality of webpages, displayed responsive to a search query of the medical condition submitted by the user, according to the maturity score, the medical condition acceptance score, and communications for the one or more search results based on a plurality of identified contextual factors, wherein adjusting the one or more search results further includes ranking, based on the maturity score and the medical condition acceptance score, the plurality of webpages displayed to the user according to positive diagnostic outcomes or successful procedures related to the medical condition identified in the communications of the respective webpages, and wherein the ranking further includes displaying the plurality of webpages to the user according to a cognitive analysis of comments, reviews, the positive diagnostic outcomes, the successful procedures related to the medical condition, and medical terminology content of each webpage being commensurate with the maturity score and the medical condition acceptance score of the user.

2. The method of claim 1, further including providing one or more suggestions for communication with the user according to the adjusted one or more search results, the maturity score, and the medical condition acceptance score.

3. The method of claim 1, further including parsing the collected data from one or more wearable devices associated with the user to identify one or more categories that includes identifying an age of the user, medical history, medical history of one or more persons associated with the user, financial conditions, status of employment, a social media user profile, social media communication patterns, favorable and unfavorable entertainment interests, food preferences, profile types and characteristics of persons associated with the user, an emotional state of the user, biometric data, behavior patterns, or a combination thereof.

4. The method of claim 3, further including assigning a weighted value to each of the one or more categories for estimating the maturity score and the medical condition acceptance score, wherein the assigned weighted values are ranked.

5. The method of claim 3, further including applying one or more selected rules for a set of the one or more categories for estimating the maturity score and the medical condition acceptance score.

6. A system for medical condition communication management, comprising:
one or more computers with executable instructions that when executed cause the system to:
collect, by one or more processors executing the executable instructions, data from one or more devices associated with a user, wherein when collecting the data, a plurality of sources are mined by the one or more devices using textual, audio, and video parsers such that the data is collected notwithstanding whether the user explicitly entered the data into the one or more devices;
train, by the one or more processors, a machine learning model using the collected data from the one or more devices, wherein training the machine learning model includes identifying a plurality of feature sets within the collected data that are each representative of characteristics of the user including medical background information of the user, activities engaged in by the user, and content consumed by the user on the one or more devices;
estimate, by the one or more processors, a maturity score and medical condition acceptance score relating to a medical condition of the user according to the collected data as analyzed in the plurality of feature sets by the trained machine learning model, wherein the maturity score represents a measure of an emotional state, age, and cognitive reasoning ability, and wherein the medical condition acceptance score represents a measure of understanding and acceptance capability of the medical condition; and
automatically adjust one or more search results of a plurality of webpages, displayed responsive to a search query of the medical condition submitted by the user, according to the maturity score, the medical condition acceptance score, and communications for the one or more search results based on a plurality of identified contextual factors, wherein adjusting the one or more search results further includes ranking, based on the maturity score and the medical condition acceptance score, the plurality of webpages displayed to the user according to positive diagnostic outcomes or successful procedures related to the medical condition identified in the communications of the respective webpages, and wherein the ranking further includes displaying the plurality of webpages to the user according to a cognitive analysis of comments, reviews, the positive diagnostic outcomes, the successful procedures related to the medical condition, and medical terminology content of each webpage being commensurate with the maturity score and the medical condition acceptance score of the user.

7. The system of claim 6, wherein the executable instructions provide one or more suggestions for communication with the user according to the adjusted one or more search results, the maturity score, and the medical condition acceptance score.

8. The system of claim 6, wherein the executable instructions parse the collected data from one or more wearable devices associated with the user to identify one or more categories that includes identifying an age of the user, medical history, medical history of one or more persons associated with the user, financial conditions, status of employment, a social media user profile, social media communication patterns, favorable and unfavorable entertainment interests, food preferences, profile types and characteristics of persons associated with the user, an emotional state of the user, biometric data, behavior patterns, or a combination thereof.

9. The system of claim 8, wherein the executable instructions assign a weighted value to each of the one or more categories for estimating the maturity score and the medical condition acceptance score, wherein the assigned weighted values are ranked.

10. The system of claim 8, wherein the executable instructions apply one or more selected rules for a set of the one or more categories for estimating the maturity score and the medical condition acceptance score.

11. A computer program product for medical condition communication management by one or more processors, the computer program product comprising a non-transitory computer-readable storage medium having computer-readable program code portions stored therein, the computer-readable program code portions comprising:
an executable portion that collects, by the one or more processors, data from one or more devices associated with a user, wherein when collecting the data, a plurality of sources are mined by the one or more devices using textual, audio, and video parsers such that the data is collected notwithstanding whether the user explicitly entered the data into the one or more devices;
an executable portion that trains, by the one or more processors, a machine learning model using the collected data from the one or more devices, wherein training the machine learning model includes identifying a plurality of feature sets within the collected data that are each representative of characteristics of the user including medical background information of the user, activities engaged in by the user, and content consumed by the user on the one or more devices;

an executable portion that estimates, by the one or more processors, a maturity score and medical condition acceptance score relating to a medical condition of the user according to the collected data as analyzed in the plurality of feature sets by the trained machine learning model, wherein the maturity score represents a measure of an emotional state, age, and cognitive reasoning ability, and wherein the medical condition acceptance score represents a measure of understanding and acceptance capability of the medical condition; and an executable portion that automatically adjusts one or more search results of a plurality of webpages, displayed responsive to a search query of the medical condition submitted by the user, according to the maturity score, the medical condition acceptance score, and communications for the one or more search results based on a plurality of identified contextual factors, wherein adjusting the one or more search results further includes ranking, based on the maturity score and the medical condition acceptance score, the plurality of webpages displayed to the user according to positive diagnostic outcomes or successful procedures related to the medical condition identified in the communications of the respective webpages, and wherein the ranking further includes displaying the plurality of webpages to the user according to a cognitive analysis of comments, reviews, the positive diagnostic outcomes, the successful procedures related to the medical condition, and medical terminology content of each webpage being commensurate with the maturity score and the medical condition acceptance score of the user.

12. The computer program product of claim 11, further including an executable portion that provides one or more suggestions for communication with the user according to the adjusted one or more search results, the maturity score, and the medical condition acceptance score.

13. The computer program product of claim 11, further including an executable portion that parses the collected data from one or more wearable devices associated with the user to identify one or more categories that includes identifying an age of the user, medical history, medical history of one or more persons associated with the user, financial conditions, status of employment, a social media user profile, social media communication patterns, favorable and unfavorable entertainment interests, food preferences, profile types and characteristics of persons associated with the user, an emotional state of the user, biometric data, behavior patterns, or a combination thereof.

14. The computer program product of claim 13, further including an executable portion that:
assigns a weighted value to each of the one or more categories for estimating the maturity score and the medical condition acceptance score, wherein the assigned weighted values are ranked; and
applies one or more selected rules for a set of the one or more categories for estimating the maturity score and the medical condition acceptance score.

* * * * *